United States Patent [19]

Kawamura et al.

[11] 4,256,835

[45] Mar. 17, 1981

[54] PROCESS FOR PREPARING CEPHAMYCIN C

[75] Inventors: Yoshimi Kawamura, Mino; Jun'ichi Shoji, Hirakata; Kouichi Matsumoto, Toyonaka, all of Japan

[73] Assignee: Shionogi & Co., Ltd., Osaka, Japan

[21] Appl. No.: 15,869

[22] Filed: Feb. 27, 1979

[30] Foreign Application Priority Data

Mar. 7, 1978 [JP] Japan ................... 53/26252

[51] Int. Cl.$^3$ ............................................. C12P 35/08
[52] U.S. Cl. ....................................... 435/48; 435/886
[58] Field of Search ........................................ 435/48

[56] References Cited

U.S. PATENT DOCUMENTS 3,977,942  8/1976  Inamine et al. .................. 435/48

Primary Examiner—Alvin E. Tanenholtz
Attorney, Agent, or Firm—Wenderoth, Lind & Ponack

[57] ABSTRACT

A novel process for preparing cephamycin C known antibiotic being useful as a medicament and veterinary drug, characterized by cultivating *Streptomyces todorominensis* sp. nov. in a suitable medium and recovering cephamycin C from the fermentation broth.

2 Claims, No Drawings

PROCESS FOR PREPARING CEPHAMYCIN C

This invention relates to a novel process for preparing antibiotic cephamycin C characterized by cultivating an antibiotic cephamycin, C-producing strain of *Streptomyces todorominensis* in a suitable medium and recovering cephamycin C from the culture broth.

Accordingly, a fundamental object of this invention is to provide a process for the fermentative preparation, cephamycin C.

Cephamycin C is one of the cephalosporins showing anti-microbial activity against gram-positive and gram-negative bacteria. More precisely, it is 7-(5-amino-5-carboxyvaleramido)-3-carbamoyloxymethyl-7-methoxy-3-cephem-4-carboxylic acid and strongly active against gram-negative bacteria as well as β-lactamase-producing Proteus with low toxicity. The details of the properties are described in J.A.C.S. 93, 2308–2310 (1971) and anti-microb. Ag. Chemother. 2, 122–131, 2, 132–135, 2, 281–286, and 2, 287–290 (1972). Thus, cephamycin C is an excellent antibiotic as noted above and can be used as a medicament and vaterinary drug.

Cephamycin C is prepared by the cultivation under controlled conditions of a hitherto undescribed strain of micro-organism which we isolated from a soil sample and have tentatively called Streptomyces PA-30177. This strain has been designated *Streptomyces todorominensis* sp. nov. and the subculture has been deposited in the Fermentation Research Institute in Japan under the accession number FERM-P 4366 and in the American Type Culture Collection, Washington, D.C., wherein it has been added to the collection of bacteria as ATCC No. 31489.

The strain Streptomyces PA-30177 has the following characteristics:

1. Morphological characteristics

Growth on Bennett's agar is good at 28° C. but no growth is observed at 50° C. and 10° C. On this medium yellowish gray aerial hyphae are formed, color of vegetative mycelium is brown and no soluble pigment is produced.

Conidia are produced on aerial hyphae and form of spore-bearing hyphae is spiral. The surface of conidia are smooth under electron microscopy.

2. Physiological characteristics

The following carbohydrates are readily utilized when included in Pridham and Gottlieb synthetic agar containing no other source of carbon: arabinose, xylose, glucose, fructose, mannitol, melibiose, galactose, lactose, mannose, maltose, inositol, rhamnose, and glycerol. Sucrose, raffinose and sorbitol do not support growth.

3. Cultural characteristics

Table I gives a more detailed description of the strain on a number of media commonly used in the study of members of the genus Streptomyces. Media were seeded by streaking and all culture were incubated at 28° C. for a 14 day period.

Streptomyces PA-30177 does not produce melanoid pigment. Milk is coagulated and peptonized. Treatment of starch agar cultures with Lugol's iodine solution indicates that the strain possesses diastatic action. Gelatin is liquiefied weakly. Tyrosinase activity is negative.

TABLE I

| | Cultural Characteristics of Streptomyces PA-30177 | | | |
|---|---|---|---|---|
| Medium | Amount of growth | Aerial mycelium and spore color | Soluble pigment | Reverse color |
| Sucrose nitrate agar | Good | light brownish gray | none | pale yellowish brown |
| Glucose asparagine agar | Good | light brownish gray | none | pale yellowish brown |
| Glycerol asparagine agar | Good | light brownish gray | none | pale yellowish brown |
| Inorganic salts starch agar | Good | yellowish gray | none | pale yellowish brown |
| Tyrosine agar | Good | light brownish gray | none | pale yellowish brown |
| Nutrient agar | Moderate | no aerial mycelium | none | pale yellowish brown |
| Yeast ex.-malt ex. agar | Good | light brownish gray | yellowish brown | yellowish brown |
| Oatmeal agar | Good | grayish yellow brown | none | pale brown |
| Bennett's agar | Good | yellowish gray | none | brown |

From the above results, it is obvious that the strain belongs to the Genus Streptomyces. Further, the strain was compared with in the morphological, cultural and physiological characteristics with many known species of Streptomyces and it has been concluded that the closest species is *Streptomyces argenteolus* disclosed in Bergey's Mannual of Determinative Bacteriology, 8th ed. 771–773 (1974) and International Journal of Systematic Bacteriology 18, 295–296 (1968). The inventors obtained the standard strain of *St. argenteolus*, KCC S-0623=ISP5226=ATCC 11009 (=23882) and directly compared it with St. PA-30177 of this invention. As the result, there are important differences as follows:

(1) The aerial mycelia of St. PA-30177 are yellowish and the color belongs to yellow color series on an inorganic salts starch agar medium and Bennett's agar medium. Those of *St. argenteolus*, however, are light brownish gray and the color belongs to gray color series. On Bennett's agar medium, the vegetative mycelia of St. PA-30177 is brown whereas those of *St. argenteolus* are graysh black.

(2) St. PA-30177 grows good utilizing melibiose and inositol whereas *St. argenteolus* utilizes neither of them completely. The growth of *St. argenteolus* is remarkable with glycerol and rhamnose whereas St. PA-30177 quite poorly grows with these carbohydrates.

(3) When cultured for 14 days at 37° C., St. PA-30177 grows good whereas *St. argenteolus* does not grow at all. On the contrary, St. PA-30177 hardly grows at 10° C. while *St. argenteolus* grows fair.

Thus, *St. argenteolus* is clearly distinguished from St. PA-30177 of this invention.

Besides, several strains have been known to produce cephamycin C. They are *Streptomyces lactamdurans* (British Pat. No. 1,321,412), *Streptomyces wadayamensis* (Dutch Pat. No. 7308948), *Streptomyces jumonjinensis* No. 3008 (Belgian Pat. No. 804341), Streptomyces P6621 (Japanese Patent Publication (Not-examined) No. 110097) and the like. The descriptions of these strains were compared with the above characteristics. It is concluded that these strains are clearly different from our strain in microbiological characteristics.

The above examination brings the conclusion that Streptomyces PA-30177 belongs to a new species and is designated *Streptomyces todorominensis* sp. nov. The strain is deposited in ATCC under the accession number 31489.

It is to be understood that this invention includes the natural and artificial mutants produced from the described strain or variants belonging to the species *Streptomyces todorominensis* as far as they can produce the antibiotic cephamycin C and cannot be clearly distinguish from *St. todorominensis*. The artificial production of mutant may be accomplished by a conventional operation such as X-ray or ultraviolet-ray irradiation, nitrogen mustards, 4-nitroquinoline N-oxide, N-methyl-N'-nitro-N-nitrosoguanidine and other mutagens.

Cephamycin C is produced by cultivating a strain of *St. todorominensis*. The process for preparing cephamycin C is explained below.

The cephamycin C-producing strain of *St. todorominensis* is cultivated in a suitable medium under aerobic conditions. The conditions of fermentation and the composition of the medium follow the usual known manner for producing antibiotics.

The composition of the medium may be varied over a very wide range. It essentially consists of carbon source, nitrogen source and inorganic elements. Vitamins and precursors may be added, if necessary. Examples of suitable carbon source are glucose, sucrose, starch, dextrin, glycerol, molasses, organic acids and the like. They may be used in single or as a mixture. Suitable nitrogen source may be exemplified for soybean meal, corn steep liquor, meat extract, yeast extract, cotton seed flour, peptone, wheat germ, ammonium sulfate, ammonium nitrate, which are used singly or as a mixture. Examples of the inorganic elements are calcium carbonate, sodium chloride, potassium chloride, magnesium sulfate, cobalt chloride, potassium phosphate and the like. They are added to the medium if the occasion demands. Liquid media are preferred for the production on a large scale. The fermentation may be proceeded for about 20 hours to about 200 hours in the usual manner as for producing antibiotics. Submerged aerobic condition is preferable for the production on a large scale, which effected for about 20 to about 100 hours.

The pH of the medium may be adjusted to about 5.5 to about 8.5. A buffering agent such as calcium carbonate may be added to the medium if the pH of the medium varies during the fermentation.

The temperature may be kept at about 20° C. to about 40° C., preferably about 28° C. to about 32° C., during the fermentation. Anti-foaming agents such as vegetable oil, lard oil, and polypropylene glycol may be added to the fermentation medium prior to or in the course of the fermentation, if excessive foaming is encountered.

Cephamycin C can be recovered from the fermentation broth by a per se conventional manner when the fermentation has finished. There may be employed any conventional method such as filtration, centrifugation, adsorption and desorption with ion-exchange resins, chromatography with various active adsorbents, extract with suitable organic solvents and the like. The methods are suitably combined to isolate cephamycin C effectively. As cephamycin C is recovered from the filtrate, it is preferred to use adsorption procedure when the fermentation is effected on a large scale. For example, the fermentation broth is filtered with filter aid and the filtrate is adsorbed on a suitable adsorbent such as active carbon, diatomaceous earth, silica gel and various ion-exchange resins. The elution is effected with a suitable solvent such as water, saline, acetone, chloroform, ethanol, butanol, and the like. The adsorption procedure may be repeated to obtain purified cephamycin C.

Thus obtained crude cephamycin C may be further purified, if desired, by a suitable method such as reprecipitation, chromatography and other various methods described above to be used for isolation.

Additionally, cephamycin C can be converted into the form of salt during the isolation procedure and also after isolation for the therapeutic and phamaceutical use.

The salts include acid-addition salts such as hydrochloride, sulfate, oxalate, succinate and the like, metal salts such as sodium salts and other pharmaceutically acceptable salts.

The antibiotic cephamycin C is useful as a medicament and veterinary drug for inhibiting the growth of gram-positive and gram-negative pathogenic microorganisms as disclosed in Antimicrob. Ag. Chemother. 2, 122-131 (1972) and 2, 287-290 (1972).

The antibiotic cephamycin C and the pharmaceutically acceptable salts thereof of this invention can be administered orally, subcutaneously, intravenously, or locally to human or animals in pharmaceutically conventional forms, e.g. injection, liquids, suspensions, emulsions, ointments, or tablets with suitable carriers, stabilizers, emulsifiers, preservatives and/or wetting agents, where a therapeutically effective amount of the active ingredient is contained. For example, cephamycin C and the pharmaceutically acceptable salts thereof can be administered orally, subcutaneously, intravenously or locally to human and domestic animals at a dosage of 0.1 mg to 100 mg per kg body weight per day according to the sensitivity of bacteria and the condition of the patients.

Further, Cephamycin C can be used as a starting material for cefoxitin and the analogs.

The following examples are given solely for the purpose of illustration and are not to be construed as limitations of the present invention, many variations of which are possible.

EXAMPLE 1

Medium A (preliminary seed medium): glucose 1.0%, N-Z amine type A (Scheffield Chemical Co., & Ltd.) 0.5%, yeast extract 0.2%, meat extract 0.1%, agar 1.5%, water (pH 7.0)

Medium B (seed medium): glucose 0.5%, soluble starch 0.5%, polypeptone 0.5%, meat extract 0.5%, yeast extract 0.25%, sodium chloride 0.25%, water (pH 0.7)

Medium C (production medium): soybean meal 1.5%, corn steep liquor 1.0%, glucose 2.0%, glycerol 0.5%, sodium chloride 0.3%, calcium carbonate 0.3%, water (pH 7.0)

Preliminary seed development is run with *Streptomyces todorominensis* (FERM-P No. 4366, ATCC No. 31489) in test-tubes containing medium A of the above composition. The seed tubes are incubated for 7 days at 28° C. Seed cultivation is effected in a 2000 ml Erlenmeyer flask containing 800 ml of medium B of the above composition. Each flask is inoculated with the preliminary seed culture of the tube and incubated for 48 hours at 28° C. on a rotary shaker.

A 30 L jar containing 18 L of medium C is inoculated with the resultant seed broth, and 8 ml of polypropylene glycol (P-2000) is added thereto. The jar is incubated for 4 days at 28°±0.5° C. with aeration of 18 L per minute and internal pressure of 0.5 kg per cm² under stirring of 200-350 r.p.m.

The thus-obtained 60 L of the fermentation broth is adjusted to pH 5.0 with 4 N hydrochloric acid and filtered with 1.6 kg of filter aid (Hyflo Super Cel). The filtrate is adjusted to pH 7.0 with 4 N sodium hydroxide solution and adsorbed on a bed (26×14 cm) of active carbon. The column is washed with water and then eluted with 50% acetone. The fractions showing antibacterial activity checked by microbial inhibition assay are collected and concentrated under reduced pressure to remove acetone. The concentrate is adsorbed on a bed (1200 ml) of BioRex-5 (Cl⁻ type) (BioRex Co., & Ltd.). The column is eluted with a 4% aqueous solution of sodium chloride. The active fractions are collected and adsorbed on a bed (9.5×48 cm) of active carbon. The column is washed with water and then eluted with 50% acetone. The active fractions are collected and concentrated to dryness under reduced pressure to give an oily syrup. Acetone is added thereto. The resultant precipitate is filtered and dried to give crude powder which has antibacterial activity. An aqueous solution of the powder is applied on a column of Cephadex G-10 (4×110 cm) (Cephadex Co., & Ltd.). The column is eluted with water. The active fractions are collected and adsorbed on a bed of HP-20 (Mitsubishi Kasei Kogyo Co., & Ltd.). The column is washed with water of pH 2.0 and then eluted with water of pH 7.0. The active fractions are lyophilized under reduced pressure to give 360 mg of crude cephamycin C as an amorphous lump.

The crude product (360 mg) is chromatographed on silica-gel thin layer plates (20×100 cm) and developed with chlorofiorm:ethanol:water (4:7:2). An active zone is eluted with 50% aqueous methanol. The eluates are concentrated under reduced pressure. The concentrate is adjusted to pH 3.0 with dilute hydrochloric acid, and adsorbed on a column (100 ml) of HP-20. The column is equilibrated beforehand with a 3% solution of sodium chloride (pH 3.0). The column is eluted with water. The active fractions are collected, then adjusted to pH 7.0 with dilute sodium hydroxide solution and lyophilized to give 140 mg of almost pure sodium salt of cephamycin C.

The product is dissolved in 2 ml of water and chromatographed on a bed (1.6×90 cm) of Biogel P-2 (Bio-Rad Lab.). The column is eluted with water containing 1% butanol. The active fractions are collected and lyophilized to give 100 mg of a sodium salt of cephamycin C as a colorless powder.

The physicochemical properties of the sodium salt are as follows:

(1) Elementary analysis: Calculated for $C_{16}H_{21}N_4SO_9Na \cdot H_2O$: C: 39.51; H, 4.76; N, 11.52; S, 6.59; Na, 4.73; Found: C: 39.50; H, 5.00; N, 11.44; S, 6.38; Na, 5.19.

(2) Ultraviolet absorption spectrum: $\lambda_{max}^{H2O}$ m$\mu$($E_1$ cm $^{1\%}$): 266 (173); 240 (142).

(3) Infrared absorption spectrum: $\nu_{max}^{KBr}$cm$^{-1}$ 1770; 1710.

(4) $^1$H-NMR spectrum: $\delta_{D_2O}^{DSS}$ ppm 1.50-2.10 (4H, m); 2.47 (2H, t-like); 3.31 (1H, d, 18); 3.53 (3H, s); 3.63 (1H, d, 18); 3.73 (1H, t-like); 4.64 (1H, d, 12.5); 4.80 (1H, d, 12.5); 5.16 (1H, s).

The product with the above properties is identified with cephamycin C depending on the description of J.A.C.S. 93 2308-2310 (1971) and also the result of direct comparative test with authentic sample of cephamycin C.

What we claim is:

1. A process for producing the antibiotic cephamycin C which comprises cultivating the antibiotic cephamycin C-producing strain of *Streptomyces todorominensis*, ATCC No. 31489 in an aqueous nutrient medium at a temperature of about 20° C. to about 40° C. for about 20 hours to about 100 hours under aerobic or submerged condition and isolating the accumulated antibiotic cephamycin C from the fermentation broth.

2. The process claimed in claim 1, wherein the isolation of the antibiotic cephamycin C is carried out by filtering the fermentation broth, and adsorbing the filtrate with a suitable adsorbent.

* * * * *